United States Patent [19]

De Felice

[11] 4,344,573

[45] Aug. 17, 1982

[54] SPRAY APPLICATOR

[75] Inventor: Wilfried De Felice, Kelkheim, Fed. Rep. of Germany

[73] Assignee: Hoechst Aktiengesellschaft, Frankfurt am Main, Fed. Rep. of Germany

[21] Appl. No.: 156,922

[22] Filed: Jun. 6, 1980

[30] Foreign Application Priority Data

Jun. 8, 1979 [DE] Fed. Rep. of Germany ... 7916475[U]

[51] Int. Cl.$^3$ .............................................. B05B 9/04
[52] U.S. Cl. ............................... 239/320; 128/203.15; 128/235; 222/562
[58] Field of Search ............................. 239/320, 331; 128/203.15, 218 C, 218 P, 235, 239, 238; 222/562; 220/306, 308

[56] References Cited

U.S. PATENT DOCUMENTS

| | | | |
|---|---|---|---|
| 2,764,981 | 10/1956 | Helmer | 128/218 C |
| 2,798,487 | 7/1957 | Ferguson | 128/218 P |
| 3,534,734 | 10/1970 | Budreck | 128/218 P X |
| 3,930,599 | 1/1976 | Brothers et al. | 222/562X |

FOREIGN PATENT DOCUMENTS 2330413  7/1977  France ................................ 128/239

*Primary Examiner*—Bruce H. Stoner, Jr.
*Assistant Examiner*—Paul A. Sobel
*Attorney, Agent, or Firm*—Curtis, Morris & Safford

[57]  ABSTRACT

A disposable spray applicator for liquid or pulverulent medicaments includes a receptacle containing the medicament and having one or more dosing chambers and is provided with a piston plug at one end, and a spray head with corresponding cap at the other end. The spray head surrounds the rim of the receptacle and is held in place by an annular sealing torus. The spray head is provided with a rectangular outlet canal, through which the medicament is sprayed at a right angle into a turbulence chamber formed by a spraying nozzle, and from there to the outside. The sealing torus has an annular groove on the surface of the receptacle facing the spray head, and an annular bead on the opposite, i.e. interior, surface. The bead mates with a correspondong groove on the piston plug to stop the action of the spray applicator when the plug has moved a distance corresponding to a measured dosage.

5 Claims, 1 Drawing Figure

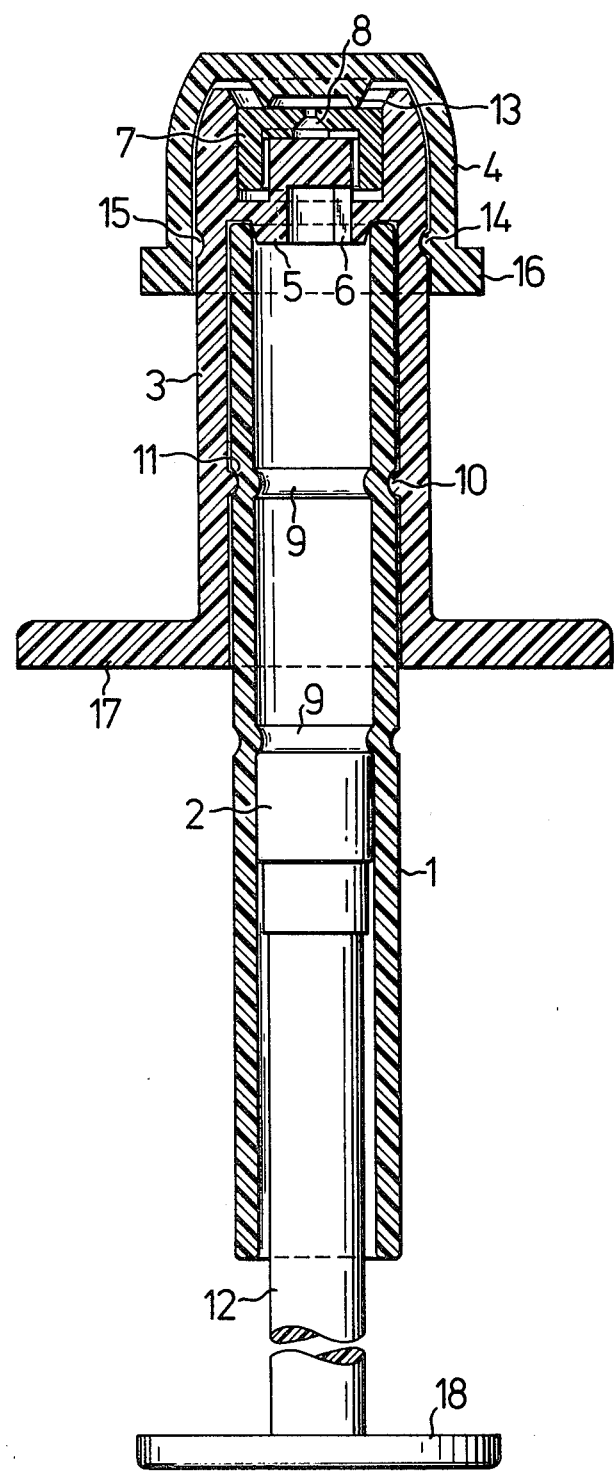

SPRAY APPLICATOR

Subject of the invention is a disposable spray applicator for liquid or pulverulent medicaments, which allows precise dosage of the medicament in the nasal region or other parts of the body.

Devices for spraying a liquid from a closed receptacle having a double-acting pump for manual operation and a spraying nozzle have been proposed previously in various embodiments. German Offenlegungsschrift No. 27,09,796, for example, describes a spray applicator consisting of a closed receptacle provided with double-acting pump for manual operation, an actuator having a recess of coaxial extension and a lateral nozzle, and a pressure-relief valve closing the pump chamber; a slide gate serving as closing device.

Spray applicators of this or similar design have a complicated technical structure which, in the case of minuscule doses in a range of about 0.1 ml, causes extreme dosage differences from one spray discharge pulse to another. It is often observed that these spray applicators "sputter" on actuation of the pump, which becomes manifest by unequal size of the ejected drops of spray. Moreover, in the hitherto known spray applicators the dosing chamber as such is often insufficiently sealed, so that the applicator has a tendency to lose a part of its contents by evaporation after only a few days storage. In such case, precise dosage of the medicament is of course impossible. There is furthermore the risk that microorganisms can migrate into sterile formulations contained in such insufficiently sealed chambers, which degrade the sterility of the medicament and may even decompose the medicament.

It is therefore an object of this invention to provide a spray applicator which overcomes these disadvantages. In accordance with the invention, it has been found that a disposable spray applicator for liquid or pulverulent medicaments is especially advantageous when a receptacle containing the medicament and having one or more dosing chambers is provided with a piston plug at one end, and a spray head with a corresponding cap at the other end; the spray head surrounding the other end of receptacle and sealing the same by means of an annular torus (which can be a bead or groove) mating with corresponding structure (groove or bead, respectively) in the head. The spray head also includes means for transmitting the sprayed medicament to the outside, which means can include a rectangular outlet canal, through which the medicament is sprayed at a right angle, a turbulence chamber, and a spraying nozzle opening to the outside. A piston rod is coupled into the piston plug.

Other features and advantages of this invention will become apparent from the ensuing description, when read in conjunction with the single drawing, in which the sole FIGURE is a sectional elevation of one embodiment of the spray applicator of this invention.

With reference to the FIGURE, a preferred embodiment of this invention includes a receptacle 1 here formed generally as a hollow cylinder, preferably of glass or plastic. A cylindrical piston plug 2 is inserted into the interior of the receptacle 1, preferably from the lower end thereof (as viewed in the FIGURE). A spray head 3 is positioned to surround the top end of the receptacle 1 (as viewed in the FIGURE) and extends along the exterior of the receptacle 1. A corresponding cap 4 is provided to cover the spray head as a protective seal from dirt or germs, and to prevent evaporation.

An annular sealing torus 5, i.e., an annular bead extends from the inside of the head 3 axially into the top end of the receptacle 1 to seal the same to the head 3.

A rectangular outlet canal 6 is provided in the head 3, through which the medicament is sprayed at right angles. A spraying nozzle 7 is situated in the top end of the head 3 and has a turbulence chamber 8 connected to the canal 6 and to the outside (when the cap 4 is removed). The head 3 and cap 4 are advantageously manufactured from plastic material. The spraying nozzle 7 is situated in a corresponding bore hole centrally positioned at the top of the spray head 3.

The piston plug 2 is girdled with one or more annular torus 9, which can be either a groove or a bead, but in this embodiment is shown to be a groove. Here two such tori 9 are provided, spaced from one another and from the top end of the plug 2 by the same distance to correspond to the same dosage amount. The spaced distances can instead by selected to be different, to correspond to different dosage amounts. The piston plug 2 has a small cylindrical protrusion at the upper end thereof. The material of the piston plug 2 is advantageously formed of rubber or other elastomer.

The receptacle 1 is correspondingly girdled by one or more annular torus 11, here each formed to have a bead on the inside of the receptacle thereby to mate with the groove tori 9. The outside of each torus 11 is then formed as groove girdling the exterior of the receptacle 1.

The spray head 3 has a cylindrical interior surface surrounding the top part of the receptacle 1, and on this surface has a sealing annular torus 10. This torus 10, to mate with the groove torus 11 in the receptacle 1, is formed as an annular bead. The torus 10 serves to hold the spray head 3 securely in place on the receptacle 1, after the head 3 and receptacle 1 are slid together.

A piston rod 12 is screwed or snapped into the piston plug 2.

The cap 4 is provided with an annular sealing cone 13, here shown having a circular bead surrounding the opening to the chamber 8, to prevent untimely discharge or leakage of medicament. The cap is held in place by cams 14 thereon which mate in a corresponding groove 15. The cams 14 catch the groove 15 when the cap 4 is pressed over the head 3.

Furthermore, the cap 4 is provided at its lower rim with a raised ring 16 in order to facilitate its removal.

The spray head has a finger support 17 at its lower end which serves to provide means by which the applicator can be held while administering the medicament.

A thumb piece 18 is disposed at the lower end of the piston rod 12.

The spray applicator is assembled in the following manner: the piston plug 12 is slid into the receptacle 1, and the medicament is charged in through the open (top) end. Subsequently, the previously assembled and sterilized spray head 3 is slid onto the open receptacle until the annular bead torus 10 catches in the exterior annular groove of the torus 11. For use of the spray applicator filled with medicament, the piston rod 12 is fastened to the piston plug 2, subsequently the cap 4 is removed, and the piston plug 2 is then pressed into the receptacle by pressure on the thumb piece 18. When the piston plug 2 reaches one of the annular tori 9 in the receptacle 1, it is compressed and subsequently, with increased pressure, pushed jerkily into the dosing chamber until it hits the next annular torus 9.

This is repeated in the same manner when emptying the next dosing chamber. When using the spray applicator, for example in the nasal region, the patient may first spray the corresponding amount of medicament into one nostril, and administer medicament to the other nostril in the same manner. As compared with the hitherto known spray applicators, the applicator of present invention has numerous advantages. It is disposable and can be used for administering several individual doses, especially at very low spray rates (for example 0.1 ml/spray pulse); fluctuation of dosage being prevented due to the precisely limiting annular tori 9 in the receptacle. Furthermore, this applicator requires considerably fewer component parts than the state-of-the-art devices. Especially this invention avoids the need for spring elements and complicated mobile sealing pistons which can be manufactured with high engineering expenditure only.

Since this spray applicator is disposable, there is no risk that undesirable clogging occurs due to crystallization of the contents or soiling of the outlet nozzle, thus preventing further withdrawal of medicament. Furthermore, several doses of below 5 ml each can be charged to a corresponding number of these spray applicators which may then be combined to a therapeutically appropriate pack. In the case where administration of varying medicament amounts is required for the treatment, this can be realized by shaping corresponding dosing chambers of different size by means of the spacing between the tori 9.

If the contents need to be maintained absolutely sterile the spray applicator is secured by the cap 4 by welding the latter to the head 3 in a so-called blister.

If the applicator is intended to be disposable, this does not degrade its service life.

Terms of orientation, as used hereinabove, to wit, top, upper, lower, etc., are used for explanation with reference to the drawing FIGURE, and should not be interpreted as limiting the invention. Further, the term torus is meant to be inclusive of annular grooves, annular beads, or equivalent structure.

Moreover, while one embodiment of this invention is described hereinabove, it should be apparent that many variations and modifications thereof are possible without departing from the scope and spirit of this invention, as defined in the appended claims.

What is claimed is:

1. A disposable spray applicator for liquid or pulverulent medicaments comprising a receptacle cylinder divided axially into one or more dosing chambers, a piston plug disposed in said receptacle cylinder, spray head means disposed at one end of said receptacle cylinder, the spray head means surrounding the cylinder at said one end and having sealing means disposed therein sealably contacting the one end of the receptacle cylinder, and nozzle means connecting to the outside; at least one annular torus girdling said receptacle cylinder to divide the same into said dosing chambers and having an inner torus face and an outer torus face on the interior and exterior sides of said receptacle cylinder, respectively; at least one mating torus in said piston plug to catch said inner torus face at the end of a predetermined dosage; and at least one mating torus in said spray head means mating with said outer torus face to ensure that the receptacle cylinder, when inserted into said spray head means, is secured therein.

2. The spray applicator as claimed in claim 1, wherein the size of the dosing chambers is determined by axial separation of the annular tori.

3. The spray applicator as claimed in claim 1, wherein said spray head means is provided with an overfitting cap having at least one cam disposed therein, and said spray head means has a corresponding groove thereon, so that said cap is held in place over said spray head means by said cam taught in said groove.

4. The spray applicator as claimed in claim 3, wherein said cap further includes a sealing cone disposed surrounding said nozzle means when the cap is in place on said spray head means.

5. The spray applicator as claimed in claim 1, wherein said nozzle means includes a spraying nozzle having an outlet, and a turbulence chamber connected therewith, and a rectangular outlet canal through which the medicament is sprayed into the turbulence chamber.

* * * * *